United States Patent
Son et al.

(10) Patent No.: US 11,020,335 B2
(45) Date of Patent: Jun. 1, 2021

(54) COSMETIC COLORING MATERIAL AND USE THEREOF

(71) Applicant: LG HOUSEHOLD & HEALTH CARE LTD., Seoul (KR)

(72) Inventors: Hong Ha Son, Daejeon (KR); Kyong Seob Kim, Daejeon (KR); Khee Hwan Choi, Daejeon (KR); Ko Eun Park, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 16/756,672

(22) PCT Filed: Oct. 15, 2018

(86) PCT No.: PCT/KR2018/012098
§ 371 (c)(1),
(2) Date: Apr. 16, 2020

(87) PCT Pub. No.: WO2019/078557
PCT Pub. Date: Apr. 25, 2019

(65) Prior Publication Data
US 2020/0281835 A1  Sep. 10, 2020

(30) Foreign Application Priority Data

Oct. 17, 2017 (KR) .................. 10-2017-0134749
Sep. 28, 2018 (KR) .................. 10-2018-0116495

(51) Int. Cl.
| | |
|---|---|
| *A61K 8/49* | (2006.01) |
| *A61K 8/87* | (2006.01) |
| *A61K 8/88* | (2006.01) |
| *A61Q 1/06* | (2006.01) |
| *C08F 222/38* | (2006.01) |
| *C08L 75/04* | (2006.01) |

(52) U.S. Cl.
CPC ............... *A61K 8/498* (2013.01); *A61K 8/87* (2013.01); *A61K 8/88* (2013.01); *A61Q 1/06* (2013.01); *C08F 222/38* (2013.01); *C08L 75/04* (2013.01); *A61K 2800/10* (2013.01); *A61K 2800/31* (2013.01); *A61K 2800/54* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 9,486,755 B2 | 11/2016 | Hasegawa et al. | |
| 2017/0319454 A1 | 11/2017 | Oohashi et al. | |

FOREIGN PATENT DOCUMENTS

| | | | | |
|---|---|---|---|---|
| JP | 5-262622 A | 10/1993 | | |
| JP | 2008-50312 A | 3/2008 | | |
| JP | 2008-120687 A | 5/2008 | | |
| KR | 10-2010-0080629 A | 7/2010 | | |
| KR | 10-2017-0085452 A | 7/2017 | | |
| KR | 10-2017-0103966 A | 9/2017 | | |
| WO | WO 2008/056688 A1 | 5/2008 | | |
| WO | WO2008056688 A1 * | 5/2008 | ............... | A61K 8/88 |

OTHER PUBLICATIONS

International Searching Authority (PCT/ISA/210) issued in PCT/KR2018/012098, dated Jan. 17, 2019.

* cited by examiner

*Primary Examiner* — Brian J Davis
(74) *Attorney, Agent, or Firm* — Birch, Stewart, Kolasch & Birch, LLP

(57) ABSTRACT

The present invention relates to a novel coloring material including a polyamide powder and/or a polyurethane powder and a water-soluble dye. The coloring material of the present invention allows a water-soluble dye to be used in anhydrous formulations. Thereby, the range of use of dyes may be widened, reflectance may be excellent, and fluorescence properties may be obtained. Accordingly, the present invention may broaden the spectrum of cosmetic coloring materials used in limited applications in the cosmetic field.

9 Claims, 6 Drawing Sheets

[FIG. 1]
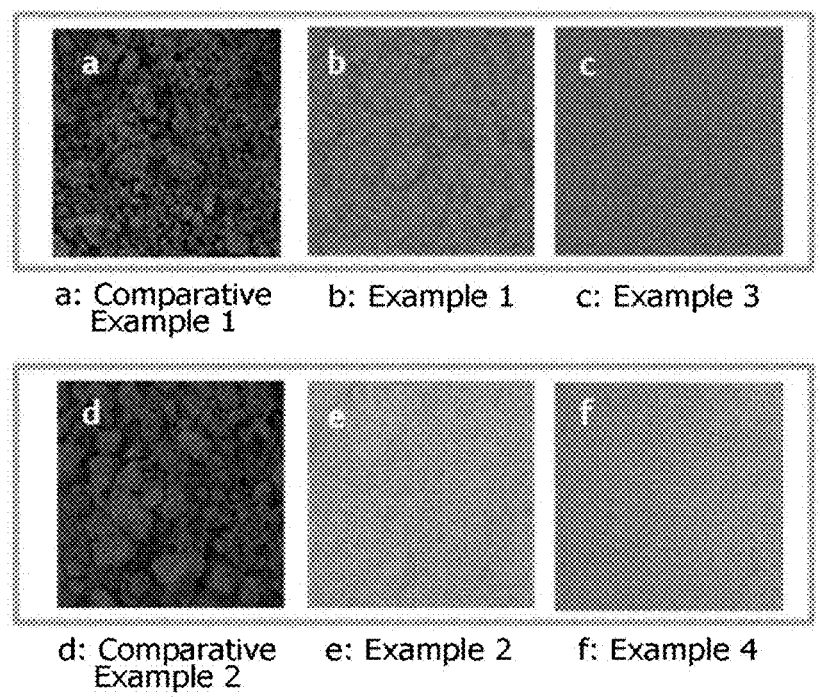
a: Comparative Example 1  b: Example 1  c: Example 3
d: Comparative Example 2  e: Example 2  f: Example 4
[FIG. 2A]
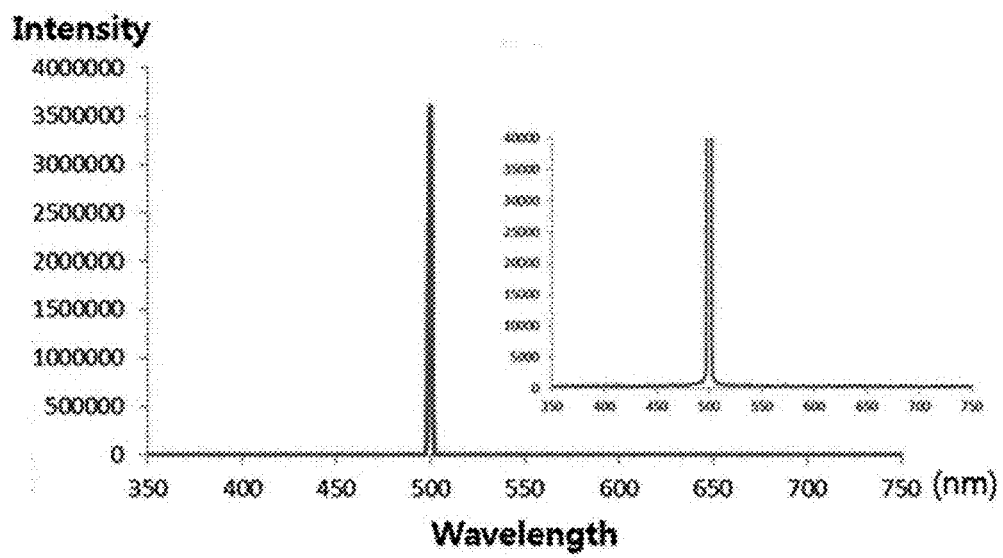

[FIG. 2B]
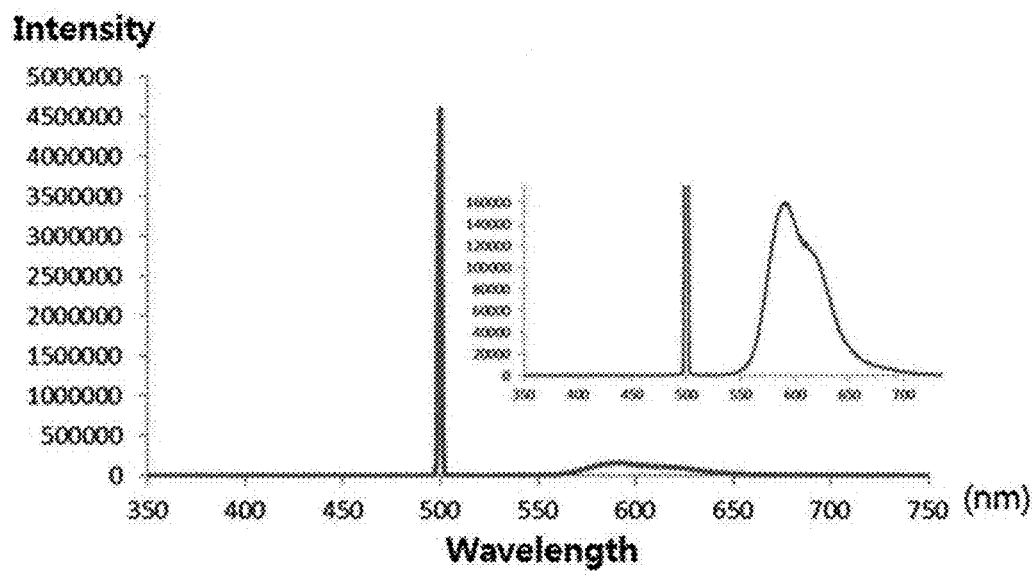
[FIG. 2C]
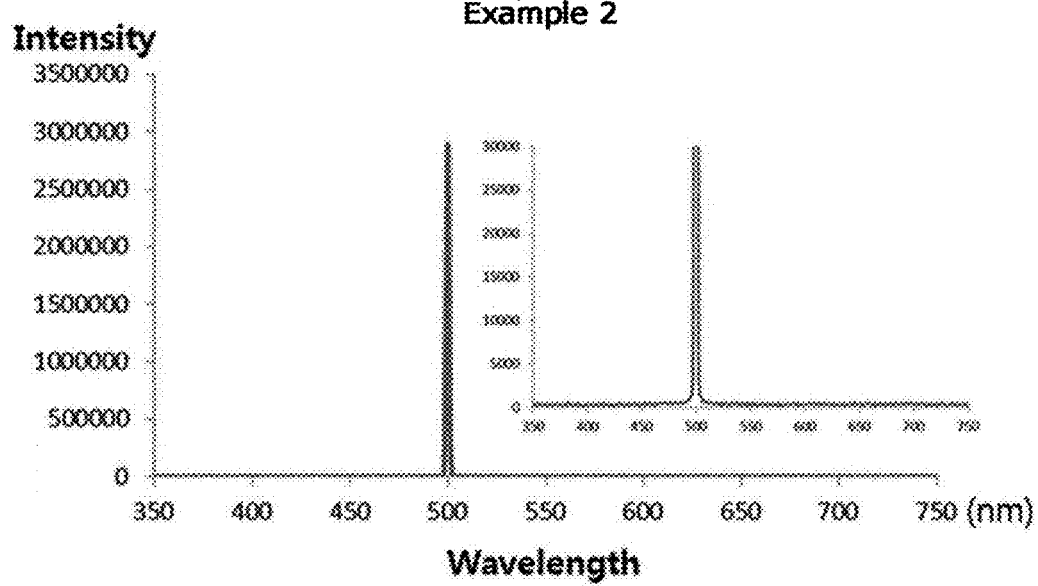

[FIG. 2D]
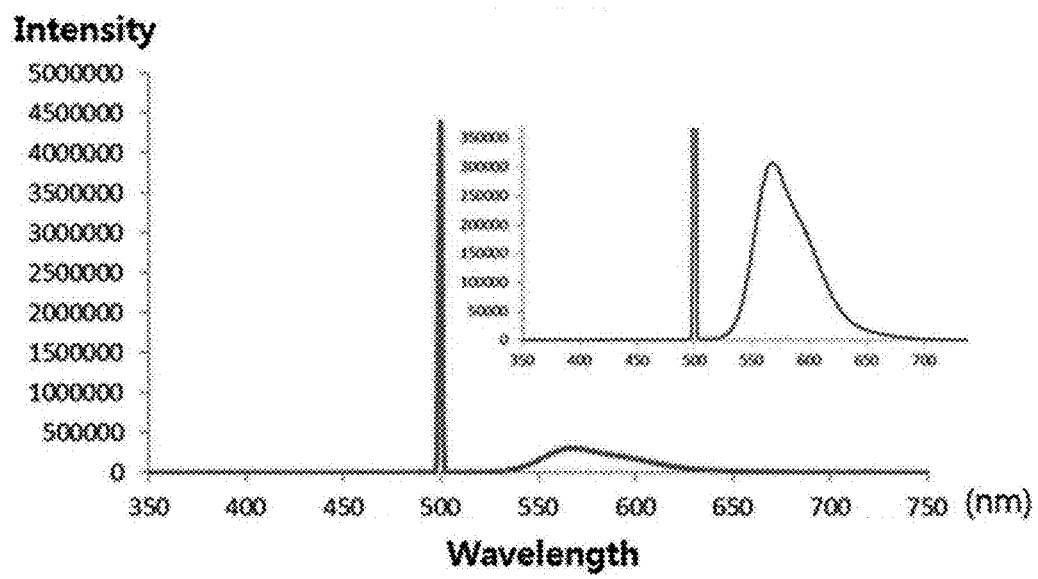
[FIG. 3A]
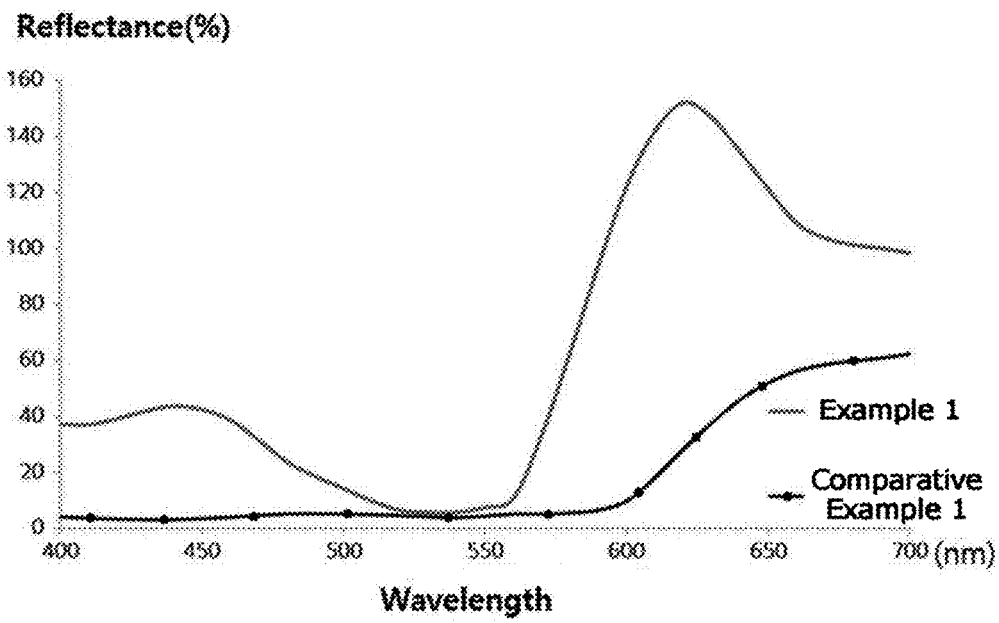

[FIG. 3B]
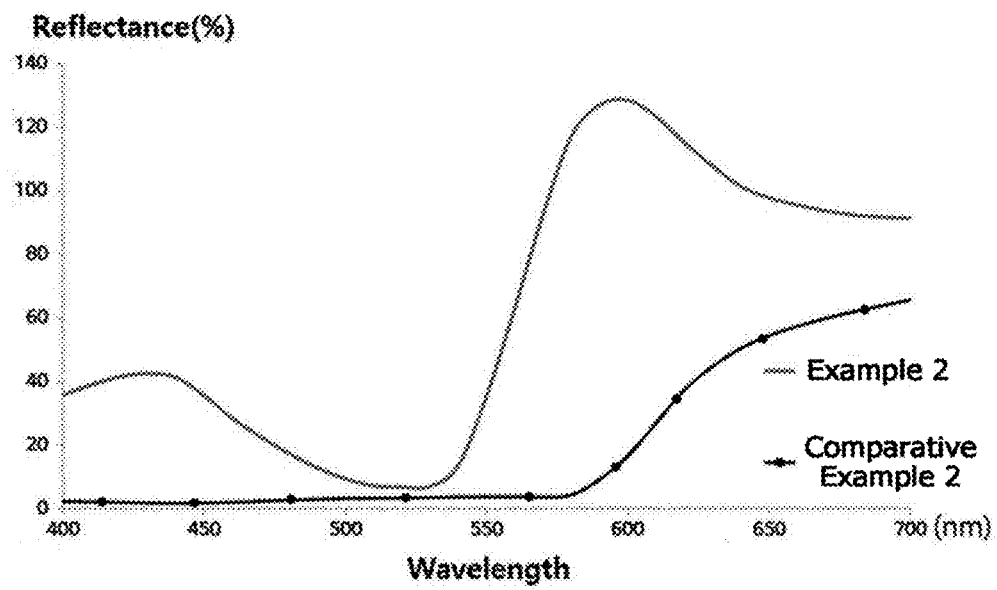
[FIG. 3C]
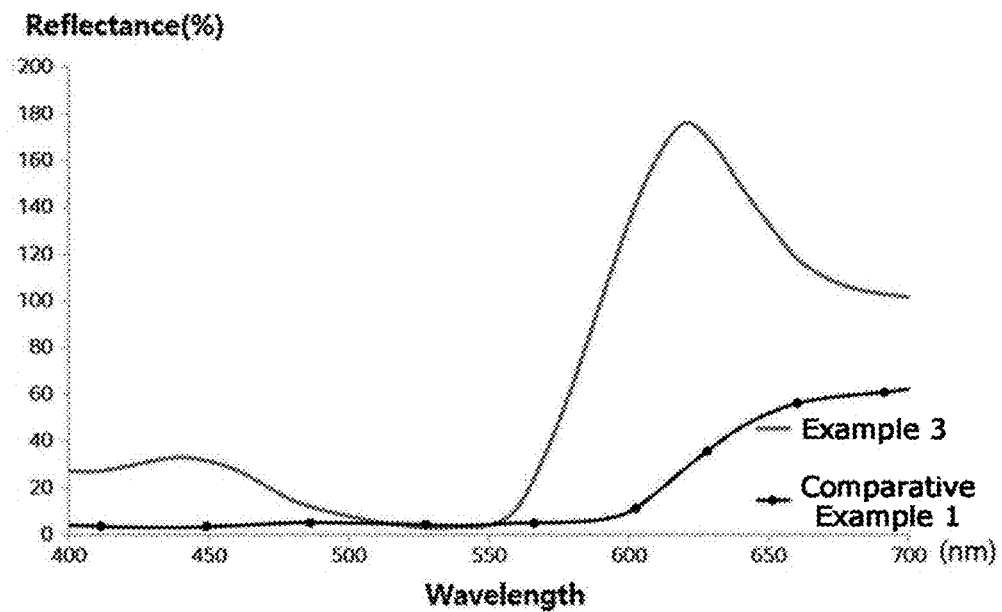

[FIG. 3D]
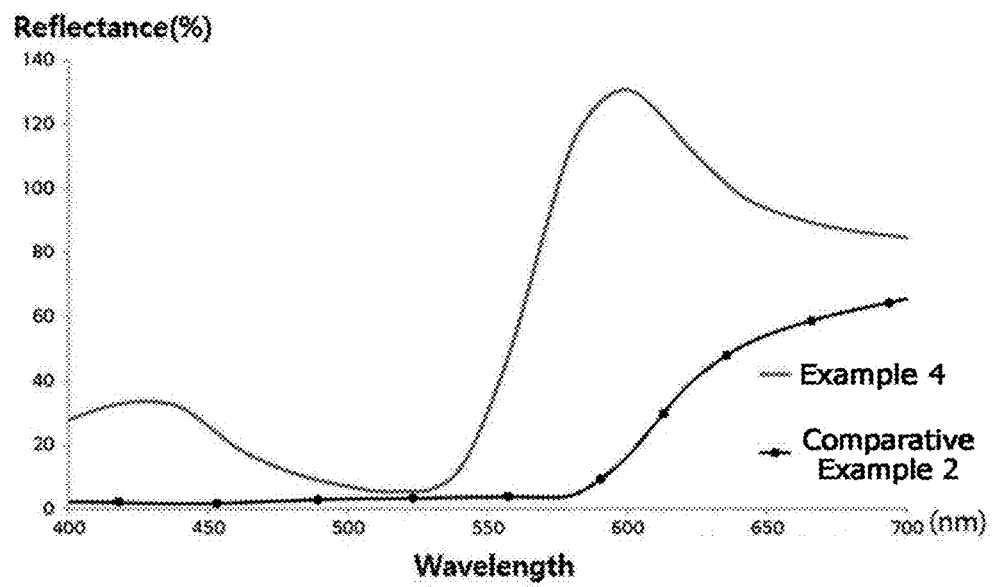
[FIG. 4]
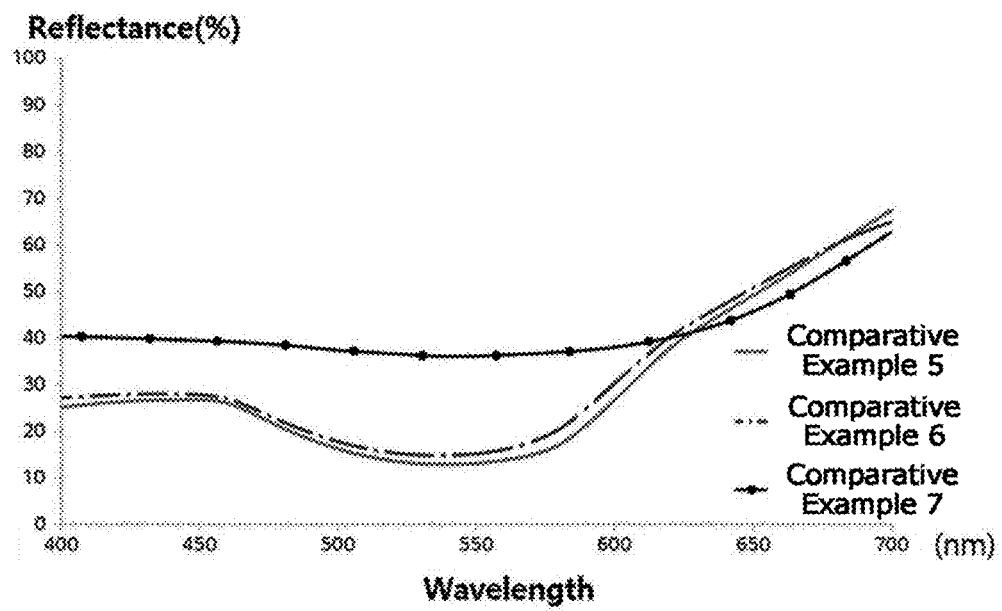

[FIG. 5A]
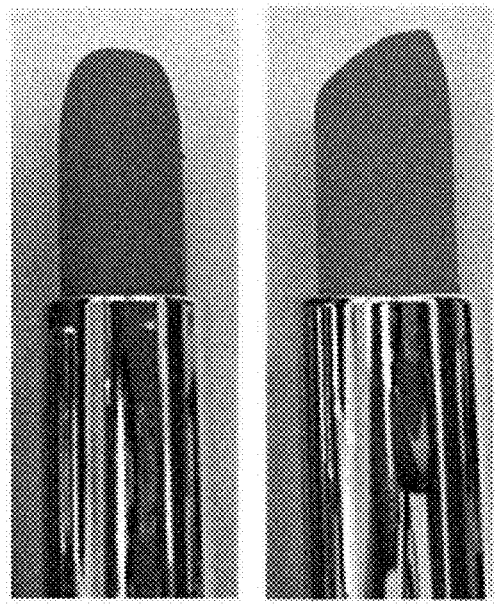
Comparative Example 8    Example 10
[FIG. 5B]
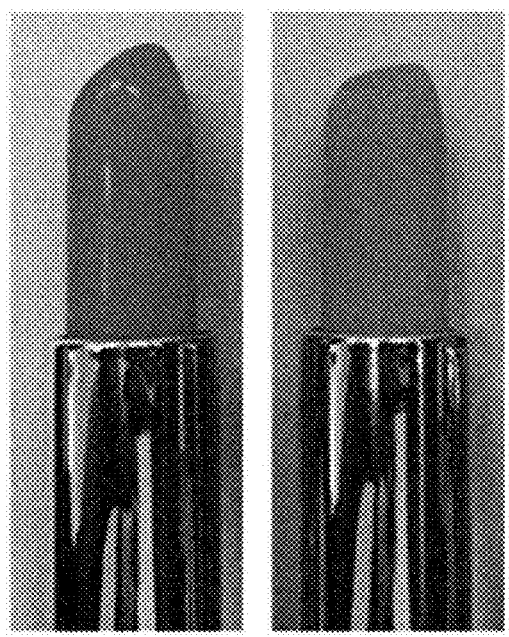
Comparative Example 9    Example 11

COSMETIC COLORING MATERIAL AND USE THEREOF

TECHNICAL FIELD

The present invention relates to a novel cosmetic coloring material and use thereof.

BACKGROUND ART

Lip cosmetics, such as lipsticks and lip glosses, and makeup cosmetics, such as cheek rouges and eye shadows, have a makeup effect that can change the impression of a user. When choosing such cosmetics, color is considered an important factor. Recently, there is increasing demand for makeup cosmetics that have vivid colors and are capable of imparting transparent impression. For example, lipsticks having high luminance and fluorescent colors are attracting attention.

In general, makeup cosmetics contain oily base materials and coloring materials (coloring agents). In this case, coloring materials are responsible for color development when makeup cosmetics are applied to the lips or skin.

Coloring materials contained in cosmetics include organic synthetic colors (also called tar colors) and inorganic pigments, and the organic synthetic colors are classified into dyes and organic pigments. In this case, the dyes include water-soluble dyes and oil-dispersible dyes, and the organic pigments include lake colors prepared by insolubilizing water-soluble or poorly water-soluble dyes.

To date, since there are few kinds of cosmetic colors that can be used in anhydrous formulations, it is difficult to realize various colors in cosmetics for lips, such as lipsticks and lip glosses. In addition, water-soluble dyes are difficult to use in anhydrous formulations due to intrinsic properties thereof.

In this regard, in Korean Patent Application Publication No. 2017-0103966, a makeup cosmetic capable of developing a fluorescent color is disclosed. However, according to the patent, the color of an oil-dispersible dye may be improved, but the cosmetic is not applicable to water-soluble dyes.

Therefore, there is a need for development of a coloring material, using limited kinds of cosmetic colors that pass all global regulations, capable of broadening the spectrum of color expression that cannot be realized with conventional dyes and a method of preparing the coloring material.

DISCLOSURE

Technical Problem

Therefore, the present invention has been made in view of the above problems, and it is one object of the present invention to provide a novel coloring material based on a water-soluble dye that is capable of being used in cosmetics of anhydrous formulations, such as lipsticks and lip glosses, a cosmetic composition, and a cosmetic composition for lips including the coloring material. According to the present invention, color limitation in conventional cosmetic coloring materials, especially cosmetics of anhydrous formulations, may be overcome.

Technical Solution

In accordance with one aspect of the present invention, provided are a coloring material and a cosmetic composition including the same.

Specifically, the present invention provides a coloring material including one or more selected from the group consisting of a polyurethane powder and a polyamide powder having a weight average molecular weight of 200,000 or more; and a water-soluble dye represented by Structural Formula 1 below.

[Structural Formula 1]

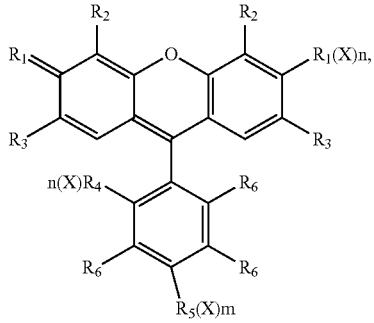

wherein $R_1$ is oxygen (O) or $N(C_2H_5)_2$, wherein, when $R_1$ is oxygen, n is 1, and when $R_2$ is $N(C_2H_5)_2$, n is 0; $R_2$ and $R_3$ are each independently hydrogen, bromine (Br), or iodine (I); $R_4$ is $COO^-$ or $SO_3^-$; $R_5$ is hydrogen, chlorine, or $SO_2^-$, wherein, when $R_5$ is hydrogen or chlorine, m is 0, and when $R_5$ is $SO_3^-$, m is 1; $R_6$ is hydrogen or chlorine; and X is aluminum, calcium, sodium, or potassium.

In accordance with another aspect of the present invention, provided is a cosmetic composition including the coloring material.

In accordance with yet another aspect of the present invention, provided is a cosmetic composition for lips including the coloring material.

Advantageous Effects

A coloring material of the present invention including a water-soluble dye; and a polyurethane-based or polyamide-based powder expresses a fluorescent color tone, has a reflectance of 100 or more, and expresses a novel color tone with very high chroma and value. According to the present invention, when the coloring material of the present invention is used, water-soluble dyes that cannot be used in conventional anhydrous formulations can be used in anhydrous formulations. Thus, the present invention can provide a cosmetic composition capable of implementing a color tone that cannot be implemented using conventional dyes or lake colors.

DESCRIPTION OF DRAWINGS

FIG. 1 includes images showing color difference between a coloring material prepared according to one embodiment of the present invention and a conventional water-soluble dye.

FIGS. 2A, 2B, 2C, and 2D are graphs showing the fluorescence analysis results of a coloring material prepared according to one embodiment of the present invention and a conventional water-soluble dye.

FIGS. 3A, 3B, 3C, and 3D are graphs showing the reflectance properties of a coloring material prepared according to one embodiment of the present invention and a conventional water-soluble dye.

FIG. 4 is a graph showing the reflectance properties of coloring materials prepared according to comparative examples of the present invention.

FIGS. 5A and 5B are images showing color difference between a lipstick manufactured using a coloring material prepared according to one embodiment of the present invention and a lipstick manufactured using a lake color.

BEST MODE

To overcome the limitations of dyes capable of being used in anhydrous formulations, the present inventors have continually tried to prepare a water-soluble dye-based coloring material that is capable of being used in anhydrous formulations. As a result, the present inventors confirmed that, when using a coloring material including a polyurethane powder and/or a polyamide powder having a weight average molecular weight of 200,000 or more; and a water-soluble dye, fluorescence properties not observed in conventional water-soluble dyes were obtained, dispersibility was excellent even in anhydrous formulations, and the coloring material was applicable to makeup products of anhydrous formulations. Based on these results, the present inventors conducted further studies to complete the present invention. According to the present invention, when the coloring material of the present invention is used, water-soluble dyes that may not be used in conventional anhydrous formulations may be used in anhydrous formulations, fluorescence properties that may not be observed in conventional dyes may be obtained, and vivid colors with high chroma and value may be expressed compared to conventional lake colors. Accordingly, the color tone of makeup cosmetics may be improved, and the range of colors that may be implemented may be widened.

Hereinafter, the present invention will be described in detail.

Since the present invention may be variously modified and may have various embodiments, exemplary embodiments and drawings of the present invention are intended to be explained and exemplified. However, these exemplary embodiments and drawings are not intended to limit the embodiments of the present invention to particular modes of practice, and all changes, equivalents, and substitutes that do not depart from the spirit and technical scope of the present invention should be understood as being encompassed in the present invention.

The present invention relates to a coloring material including a polyurethane powder and/or a polyamide powder having a weight average molecular weight of 200,000 or more; and a water-soluble dye.

The present invention allows the water-soluble dye to be used in anhydrous formulations through the coloring material, thereby providing a cosmetic that expresses a color of an extended spectrum that could not be achieved in anhydrous formulations up to now. Thus, the coloring material may be a cosmetic coloring material.

The coloring material of the present invention may have a reflectance of 100 or more. Reflectance indicates the degree to which a coloring material reflects light depending on wavelength. Reflectance exceeding 100 means that the quantity of light reflected is more than the quantity of light absorbed. That is, coloring materials having a reflectance of 100 or more may express more vivid colors and thus may be suitable as components of cosmetics. In one embodiment of the present invention, the coloring material of the present invention has a reflectance of greater than 100 at a wavelength of 600 nm to 620 nm.

In addition, the coloring material of the present invention may have fluorescence expression properties.

The coloring material of the present invention may be obtained by combining a polyurethane powder and/or a polyamide powder having a weight average molecular weight of 200,000 or more and a water-soluble dye, or by applying a water-soluble dye to the surface of a polyurethane powder and/or a polyamide powder having a weight average molecular weight of 200,000 or more. As compared to a cosmetic composition simply including the powder and the water-soluble dye, a cosmetic composition including the coloring material of the present invention obtained by applying the water-soluble dye to the surface of the powder may have higher reflectance, and may have fluorescence expression properties. In addition, the coloring material may be efficiently dispersed even in cosmetics of anhydrous formulations.

In the present invention, the water-soluble dye refers to a dye having a property of dissolving in water-soluble solvents among dyes suitable for cosmetics, and refers to a dye having hydrolyzable properties among dyes suitable for cosmetics as defined by the Korea Food and Drug Administration.

Preferably, the water-soluble dye of the present invention may be represented by Structural Formula 1 below. The compound represented by Structural Formula 1 may be a salt compound.

[Structural Formula 1]

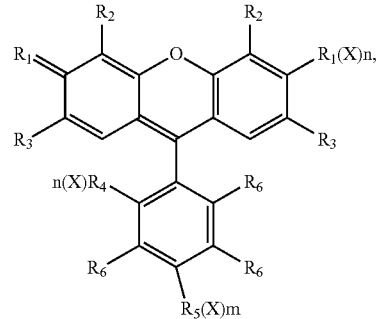

wherein $R_1$ is oxygen (O) or $N(C_2H_5)_2$, wherein, when $R_1$ is oxygen, n is 1, and when $R_1$ is $N(C_2H_5)_2$, n is 0; $R_2$ and $R_3$ are each independently hydrogen, bromine (Br), or iodine (I); $R_4$ is $COO^-$ or $SO_3^-$; $R_5$ is hydrogen, chlorine, or $SO_3^-$, wherein, when $R_5$ is hydrogen or chlorine, m is 0, and when $R_5$ is $SO_3^-$, m is 1; $R_6$ is hydrogen or chlorine; and X is aluminum, calcium, sodium, or potassium.

In Structural Formula 1, when $R_1$ is oxygen (O), $R_4$ may be $COO^-$, and $R_5$ may be hydrogen or chlorine. In this case, one of two $R_2$ may represent an ionic form of $O^-$.

Alternatively, in Structural Formula 1, when $R_1$ is $N(C_2H_5)_2$, $R_4$ and $R_5$ may be $SO_3^-$. In this case, one of two $R_1$ may represent an ionic form of $N(C_2H_5)_2+$. In the present invention, a water-soluble dye having a structure represented by Structural Formula 1 may be combined with a polyurethane powder and/or a polyamide powder to obtain a novel coloring material. The color properties of the coloring material may be improved compared to conventional water-soluble dyes. Compared to conventional lake colors, when the coloring material is included in cosmetics, colors with high value and chroma may be expressed. In particular, since the coloring material has excellent dispersibility even in anhydrous formulations, the coloring material may efficiently be used in cosmetic compositions of anhydrous formulations such as lipsticks. In addition, the spectrum of colors that may be expressed in conventional anhydrous formulations may be broadened.

Preferably, the water-soluble dye includes one or more selected from the group consisting of Pigment Red No. 104-1, Pigment Red No. 104-2, Pigment Red No. 103-1, Pigment Red No. 230-2, Pigment Orange No. 207, Pigment Red No. 106, Pigment Yellow No. 202-1, and Pigment Yellow No. 202-2.

Pigment Red No. 104-1 may be a disodium salt of 9-(3,4,5,6-tetrachloro-2-carboxyphenyl)-6-hydroxy-2,4,5,7-tetrabromo-3H-xanthene-3-one, and may be represented by Chemical Formula 1 below.

[Chemica Formula 1]

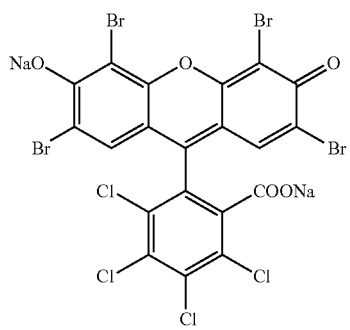

Pigment Red No. 104-2 may be a dipotassium salt of 9-(3,4,5,6-tetrachloro-2-carboxyphenyl)-6-hydroxy-2,4,5,7-tetrabromo-3H-xanthene-3-one, and may be represented by Chemical Formula 2 below.

[Chemica Formula 2]

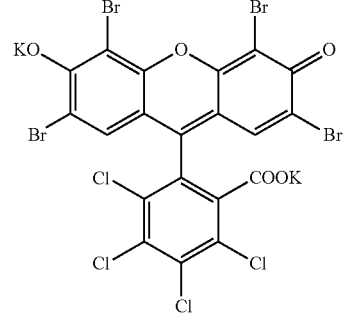

Pigment Red No. 103-1 may be a disodium salt of 9-(2-carboxyphenyl)-6-hydroxy-2,4,5,7-tetrabromo-3H-xanthene-3-one, and may be represented by Chemical Formula 3 below.

[Chemica Formula 3]

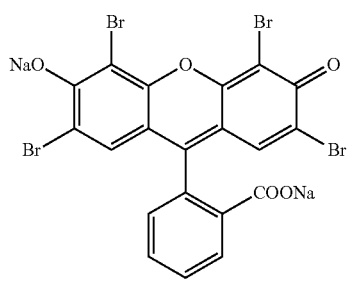

Pigment Red No. 230-2 may be a dipotassium salt of 9-(2-carboxyphenyl)-6-hydroxy-2,4,5,7-tetrabromo-3H-xanthene-3-one, and may be represented by Chemical Formula 4 below.

[Chemical Formula 4]

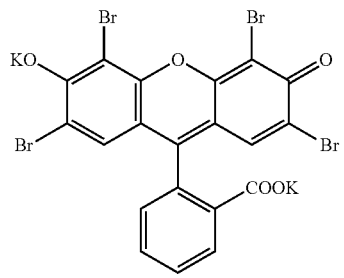

Pigment Orange No. 207 may be a disodium salt of 9-(2-carboxyphenyl)-6-hydroxy-4,5-diiodine-3H-xanthene-3-one, and may be represented by Chemical Formula 5 below.

[Chemica Formula 5]

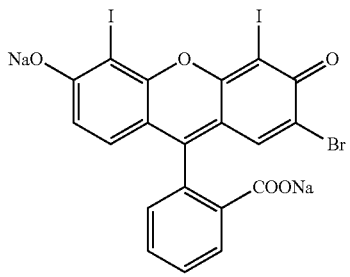

Pigment Red No. 106 may be a monosodium salt of 2-[[N,N-diethyl-6-(diethylamino)-3H-xanthene-3-imino]-9-yl]-5-sulfobenzenesulfonate, and may be represented by Chemical Formula 6 below. Pigment Red No. 106 is also referred to as Acid Pigment Red No. 52.

[Chemical Formula 6]

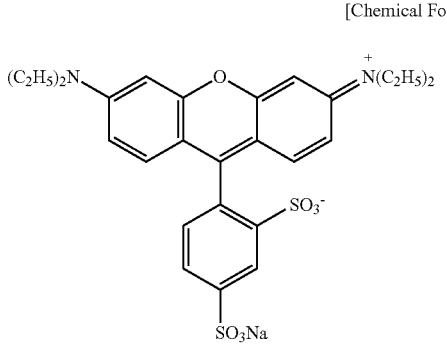

Pigment Yellow No. 202-1 may be a disodium salt of 9-(2-carboxyphenyl)-6-hydroxy-3H-xanthene-3-one, and may be represented by Chemical Formula 7 below.

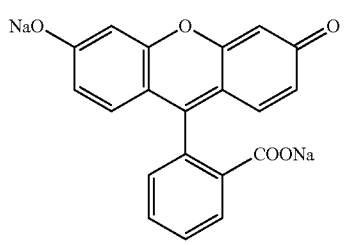

[Chemical Formula 7]

Pigment Yellow No. 202-2 may be a dipotassium salt of 9-ortho-carboxyphenyl-6-hydroxy-3-isoxanthone, and may be represented by Chemical Formula 8 below.

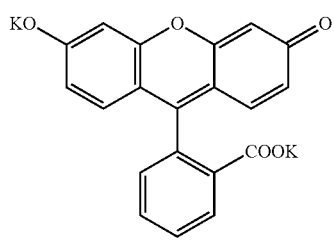

[Chemical Formula 8]

The water-soluble dye of the present invention has a structure represented by Structural Formula 1. With this structural feature, although the water-soluble dye of the present invention is a water-soluble dye, by combining the water-soluble dye and a polyurethane powder and/or a polyamide powder, the coloring material having fluorescence expression properties may be obtained.

In the present invention, the powder refers to a collection of solid particles or fine solid particles, and may be used in combination with powders commonly used in the art to which the present invention pertains.

In the present invention, the polyurethane powder includes all polyurethane-based powders, and may be a polymer of isocyanate group/OH group.

As a specific example, the polyurethane powder may include one or more selected from the group consisting of a hexamethylene diisocyanate (HDI)/trimethylol hexyllactone crosspolymer; and a hexamethylene diisocyanate (HDI)/polypropylene glycol (PPG)/polycaprolactone crosspolymer, without being limited thereto.

In consideration of the physical properties of compositions to be added and ease of use, the polyurethane powder may further include organic/inorganic particles such as silica or polymethylsilsesquioxane within a content range that does not affect the properties of the polyurethane powder.

In addition, commercially available polyurethane powders may be used as the polyurethane powder of the present invention. For example, the polyurethane powder may include D-400 (Toshiki Co.), EPU-2X (hexamethylene diisocyanate/trimethylol hexyllactone crosspolymer & polymethyl methacrylate, silica, SUNJIN BEAUTY SCIENCE Co.), and KSP-101 (SHINETSU Co.), without being limited thereto.

The polyurethane powder may have a weight average molecular weight of 5,000 to 300,000, preferably 7,000 to 100,000. Within this range, a coloring material having a reflectance of 100 or more, high value and chroma, and fluorescence expression properties may be provided.

In addition, the polyurethane powder may have an average particle diameter of 5 μm to 30 μm, preferably 10 μm to 20 μm. Within this range, a coloring material having a reflectance of 100 or more and fluorescence expression properties may be provided.

In the present invention, the polyamide powder may have a weight average molecular weight of 200,000 or more. When the molecular weight of the polyamide powder is less than 200,000, reflectance may be lowered when the polyamide powder is reacted with the water-soluble dye of the present invention. In addition, since the polyamide powder of the present invention has a high molecular weight of 200,000 or more, the polyamide powder has low oil absorption ability, thereby weakening the thickening effect of a composition. In addition, when the polyamide powder is included in a cosmetic composition, the gloss of a cosmetic may be improved. In addition, since a coloring material having a high molecular weight may be used, manufacture of cosmetics may be easily controlled, and the manufacturing process including dispersion may be easily performed.

As the polyamide powder, nylon powders may be used. For example, the polyamide powder may include one or more selected from the group consisting of nylon-6, nylon-11, nylon-12, nylon-66, and copolymers thereof. When the condition of weight average molecular weight is satisfied, the type of nylon is not limited. For example, the copolymer may be a copolymer of nylon-6 and nylon-12, without being limited thereto.

Preferably, the coloring material of the present invention includes the water-soluble dye; and the polyurethane powder. Since the coloring material of the present invention including the water-soluble dye and the polyurethane powder has a very high reflectance, when the coloring material is included in cosmetics, color expression properties may be further improved, and cosmetics having fluorescence properties may be provided.

Preferably, the coloring material of the present invention includes the water-soluble dye; and the polyamide powder having a weight average molecular weight of 200,000 or more. The coloring material of the present invention including the water-soluble dye and the polyamide powder having a weight average molecular weight of 200,000 or more has low oil absorption ability, thereby weakening the thickening effect of a composition. Thus, when the coloring material is included in cosmetics, gloss of the cosmetics may be improved.

Preferably, in the coloring material of the present invention, the powder is preferably included in an amount of 80 to 99.99% by weight, more preferably 90 to 99.9% by weight, most preferably 95 to 99.9% by weight, based on total weight of the coloring material. When the powder is included in an amount of greater than 99.99% by weight, the intensity of the color tone of the coloring material may be relatively reduced. When the powder is included in an amount of less than 80% by weight, it is difficult to use the coloring material in a makeup cosmetic composition of an anhydrous formulation, and the distinctiveness of a color tone may be degraded.

In the coloring material of the present invention, the water-soluble dye is preferably included in an amount of 0.01 to 20% by weight, more preferably 0.1 to 10% by weight, most preferably 0.1 to 5% by weight, based on total weight of the coloring material. When the dye is included in an amount of less than 0.01% by weight, color development ability may be reduced. Thus, when a makeup cosmetic composition is prepared, it is difficult to use an appropriate amount. When the dye is included in an amount of greater than 20% by weight, it is difficult to use the dye in anhydrous formulations. In addition, in terms of color tone, difference between the coloring material of the present invention and conventional dyes may be reduced.

The coloring material of the present invention has an advantage in that the coloring material broadens the spectrum of colors that may be used in cosmetic compositions. The present invention relates to a cosmetic composition including the coloring material.

Preferably, the cosmetic composition is a cosmetic composition of an anhydrous formulation. In addition, given that the cosmetic composition includes the coloring material, the cosmetic composition may be a cosmetic composition for makeup or lips. In the case of the cosmetic composition including the coloring material of the present invention, since the coloring material of the present invention has excellent reflectance and a property of expressing a fluorescent color, the cosmetic composition may have high value and chroma as compared to conventional lake colors. Accordingly, when the cosmetic composition including the coloring material of the present invention is used to manufacture makeup products for eye, mouth, or the like, the makeup products may have excellent color expression properties.

In the cosmetic composition of the present invention, the coloring material may be included in an amount of 0.1 to 50% by weight. Depending on the specific use of the cosmetic composition, the content of the coloring material may vary. For example, when the cosmetic composition is used as the composition of a cosmetic for lips, the coloring material of the present invention may be included in an amount of 5 to 50% by weight or 15 to 35% by weight.

In addition to the above-described components, the cosmetic composition of the present invention may include one or more of oils and fats, moisturizers, softeners, surfactants, organic and inorganic pigments, organic powders, UV absorbers, preservatives, thickeners, disinfectants, antioxidants, plant extracts, pH adjusters, alcohols, colors, fragrances, blood flow stimulants, cool-absorbents, and waxes, which are commonly included in cosmetic compositions, without being limited thereto.

In particular, when the cosmetic composition of the present invention is the composition of a cosmetic for lips, the cosmetic composition may further include one or more selected from the group consisting of waxes, oils, colors, and other additives.

As the wax, candelilla wax, carnauba wax, ceresin, paraffin, cocoa butter, polyethylenes, microcrystalline wax, ozocerite, beeswax, and synthetic wax may be used, without being limited thereto. In the composition of a cosmetic for lips according to the present invention, wax may be included in an amount of 3 to 20% by weight, without being limited thereto.

As the oil component, mineral oils; animal oils such as squalene and lanoline; plant oils such as sunflower seed oil, avocado oil, jojoba oil, olive oil, and castor oil; and synthetic oils such as diphenylsiloxy phenyl trimethicone, isopropyl myristate, isopropyl palmitate, cetyl ethylhexanoate, cetyl myristate, polybutene, polyisobutene, hydrogenated polyisobutene, polyols, tri-2-ethylhexyl glycerin, triglyceride-based oils, octyldodecanol, and diisostearyl malate may be used, without being limited thereto.

In addition, in the present invention, the cosmetic composition, in particular, a cosmetic composition for lips, may further include conditioning agents, oily raw materials, moisturizers, antioxidants, UV absorbers, preservatives, or fragrances within a range that does not affect the effect of the present invention.

The cosmetic composition, in particular, a cosmetic composition for lips, may be subjected to processes such as heating, mixing, and stirring in accordance with common preparation methods to manufacture lipsticks, lip glosses, lip balms, or lip liners.

In addition, the present invention provides a method of manufacturing a cosmetic for lips, the method including a step of preparing a coloring material by mixing one or more selected from the group consisting of a polyurethane powder and a polyamide powder having a weight average molecular weight of 200,000 or more and a water-soluble dye; and a step of adding the coloring material to a cosmetic composition.

The coloring material of the present invention prepared by mixing one or more selected from the group consisting of a polyurethane powder and a polyamide powder having a weight average molecular weight of 200,000 or more and a water-soluble dye may exhibit excellent dispersibility even in anhydrous formulations. In particular, the coloring material may have excellent fluorescence properties that may not be achieved by conventional dyes. Thus, when the coloring material is used, cosmetics having a good color tone and excellent expression properties may be manufactured.

In the method of manufacturing a cosmetic for lips according to the present invention, when the polyamide powder has a weight average molecular weight of 200,000 or more, oil absorption ability may be lowered, thereby weakening the thickening effect of a composition. Thus, the gloss of the cosmetic for lips may be improved. In addition, due to ease of dispersion, cosmetic manufacturing efficiency may be improved.

Hereinafter, the present invention will be described in detail through preparation examples and experimental examples. The following preparation examples and experimental examples are only for illustration of the present invention, and the scope of the present invention is not limited thereto.

Preparation Example 1

Preparation of Coloring Material

Preparation Example 1-1

Preparation of Coloring Material Using Powder

A water-soluble dye was dissolved in a solvent composed of purified water and ethanol. Nylon-12 (ANYBES, average particle diameter: 6 to 9 µm, molecular weight: 300,000, SH Energy Chemistry Co., see Table 1) as a polyamide-based powder; and a polyurethane-based HDI/trimethylol hexyl-lactone crosspolymer and silica (TOSHIKI Co., plastic powder D-400, average particle diameter: 12 to 18 µm, molecular weight: 10,000 or more, see Table 1) or silica (Sunjin Chemical Co., SUNSIL-130, average particle diameter: 7 µm, see Table 2) were added to the solvent in which the water-soluble dye had been dissolved. Then, mixing reaction was performed while stirring the mixture at 1,000 rpm for 10 minutes using a Disper mixer. The mixing ratios of Pigment Red No. 104-1 or Pigment Red No. 103-1 as the water-soluble dye to the powder are shown in Table 1. After mixing reaction, the solvent was evaporated to obtain a coloring material.

TABLE 1

| Components (wt %) | Example 1 | Example 2 | Example 3 | Example 4 | Example 5 | Example 6 | Example 7 | Example 8 | Example 9 |
|---|---|---|---|---|---|---|---|---|---|
| HDI/trimethylol hexyllactone crosspolymer, silica | — | — | 99.0 | 99.0 | 9.9 | 29.7 | 49.5 | 69.3 | 89.1 |
| Nylon-12 | 99.0 | 99.0 | — | — | 89.1 | 69.3 | 49.5 | 29.7 | 9.9 |
| Pigment Red No. 104-1 | 1.0 | — | 1.0 | — | 1.0 | 1.0 | 1.0 | 1.0 | 1.0 |
| Pigment Red No. 103-1 | — | 1.0 | — | 1.0 | — | — | — | — | — |
| Total | 100 | 100 | 100 | 100 | 100 | 100 | 100 | 100 | 100 |

TABLE 2

| Components (wt %) | Comparative Example 1 | Comparative Example 2 | Comparative Example 3 | Comparative Example 4 |
|---|---|---|---|---|
| Silica | — | — | 99.0 | 99.0 |
| Pigment Red No. 104-1 | 100.0 | — | 1.0 | — |
| Pigment Red No. 103-1 | — | 100.0 | — | 1.0 |
| Total | 100 | 100 | 100 | 100 |

Preparation Example 1-2

Preparation of Coloring Material Including Pigment Red No. 227

A coloring material including a dye (Pigment Red No. 227) was prepared using nylon-12 and a polyurethane-based powder or silica in the same manner as in Example 1-1 except that Pigment Red No. 227 was used as the water-soluble dye.

[Pigment Red No. 227]

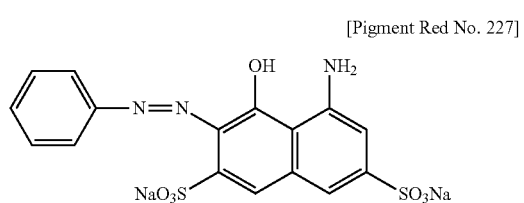

TABLE 3

| Components | Comparative Example 5 | Comparative Example 6 | Comparative Example 7 |
|---|---|---|---|
| HDI/trimethylol hexyllactone crosspolymer, silica | 99.0 | — | — |
| Nylon-12 | — | 99.0 | — |
| Silica | — | — | 99.0 |
| Pigment Red No. 227 | 1.0 | 1.0 | 1.0 |
| Total | 100 | 100 | 100 |

Experimental Example 1

Evaluation of Properties of Novel Coloring Material

To evaluate the properties of the coloring material prepared according to Preparation Example 1-1, color difference among the water-soluble dye (Pigment Red No. 104-1) of Comparative Example 1, the coloring material (a polyamide powder having a molecular weight of 300,000+ Pigment Red No. 104-1) of Example 1, and the coloring material (a polyurethane powder+Pigment Red No. 104-1) of Example 3 was confirmed by visual observation. In the same manner, color difference among Comparative Example 2 (Pigment Red No. 103-1), the coloring material (a polyamide powder having a molecular weight of 300,000+ Pigment Red No. 103-1) of Example 2, and the coloring material (a polyurethane powder+Pigment Red No. 103-1) of Example 4 was confirmed. The obtained results are shown in FIG. 1.

As shown in FIG. 1, it can be seen that color difference between the coloring materials of Examples 1 to 4 of the present invention and the conventional water-soluble dye of Comparative Example 1 or 2 is significant, and in particular, a fluorescent color tone is observed only in the coloring materials of Examples 1 to 4 of the present invention.

In addition, the fluorescence of the coloring materials of Comparative Examples 1 and 2 and Examples 3 and 4 was analyzed using a time-resolved fluorescence spectrophotometer. Excitation was performed at 500 nm for each treatment, and light intensity was measured in the visible light region.

As a result, as shown in FIGS. 2A to 2D, upon irradiation of light having a wavelength of 500 nm, the coloring materials of Examples 3 and 4 emitted light. On the other hand, in Comparative Examples 1 and 2, no light other than light emitted from a light source was observed. Accordingly, it can be seen that, unlike Comparative Example 1 (Pigment Red No. 104-1) or Comparative Example 2 (Pigment Red No. 103-1), Examples 3 and 4 have the properties of a fluorescent coloring material that emits light after receiving light energy.

Experimental Example 2

Analysis of Reflectance of Dye

Light reflectance depending on wavelength may be measured, and, based on the results, the fluorescence color tone of a coloring material may be verified. Thus, the light reflectance of the dyes of Examples 1 to 9 and Comparative Examples 1 to 4 depending on wavelength was measured using a MINOLTA CM512M3 color-difference meter. Specifically, reflectance was measured at 600 nm or 620 nm, and the results are shown in Table 4.

TABLE 4

|  | Example 1 | Example 2 | Example 3 | Example 4 | Example 5 | Example 6 | Example 7 | Example 8 | Example 9 |
|---|---|---|---|---|---|---|---|---|---|
| Reflectance | 152 (620 nm) | 129 (600 nm) | 176 (620 nm) | 131 (600 nm) | 155 (620 nm) | 159 (620 nm) | 165 (620 nm) | 169 (620 nm) | 173 (620 nm) |

TABLE 5

|  | Comprative Example 1 | Comprative Example 2 | Comprative Example 3 | Comprative Example 4 | Comprative Example 5 | Comprative Example 6 | Comprative Example 7 |
|---|---|---|---|---|---|---|---|
| Reflectance | 28 (620 nm) | 15 (600 nm) | 85 (620 nm) | 70 (600 nm) | 44 (620 nm) | 42 (620 nm) | 42 (620 nm) |

As a result, as shown in FIGS. 3A to 3D, the conventional water-soluble dye according to Comparative Example 1 or 2 that was not modified with a powder exhibited a reflectance of less than 100 in all wavelengths, and the coloring material including silica according to Comparative Example 3 or 4 also exhibited a reflectance of less than 100. Thus, it was confirmed that desired reflectance properties were not obtained in Comparative Examples. However, all of the coloring materials of Examples 1 to 9 exhibited a reflectance of 100 or more at a wavelength of 620 nm to 600 nm. These results indicated that, in the coloring materials of Examples 1 to 9, the quantity of light reflected was greater than the quantity of light absorbed, and thus all of the coloring materials were fluorescent coloring materials. In particular, under the same conditions, the coloring material according to Example 3 or 4 that was modified with a polyurethane-based powder exhibited an increased reflectance as compared to the case of using a polyamide coloring material. In addition, when a lipstick was manufactured using the coloring material of the present invention, the same tendency was observed.

In addition, as shown in Table 5 or FIG. 4, the coloring material including Pigment Red No. 227 had a reflectance of less than 100 even though modification was performed in the same manner, and did not exhibit the properties of a fluorescent coloring material when confirmed by visual observation. Thus, it can be seen that, only for dyes having a structure that satisfies Structural Formula 1, the properties of a fluorescent coloring material may be obtained through modification with the powder of the present invention.

Preparation Example 2

Manufacture of Cosmetics of Anhydrous Formulations

It was confirmed that the coloring materials of Examples 1 to 4 had the properties of a fluorescent coloring material. Based on this result, to confirm whether the coloring material might be used in an anhydrous formulation, lipsticks were manufactured using the coloring materials of Examples 3 and 4. To compare color expression properties in products of anhydrous formulations, lipsticks were manufactured using lake colors, Red28 Lake and Red22 Lake for water-soluble dyes, Pigment Red No. 104-1 and Pigment Red No. 103-1, respectively.

Wax and oil components shown in Table 6 were heated to melt the wax, and were mixed by stirring at 1,000 rpm for 10 minutes using a Disper mixer. Then, a color was added thereto, and additional stirring was performed at 1,000 rpm for 10 minutes using a Disper mixer. Then, the Disper mixer was removed, and the mixture was poured into a lipstick mold, followed by cooling to complete manufacture of a lipstick. As the polyurethane powder (HDI/trimethylol hexyllactone crosspolymer, silica), powder having the same conditions as in Preparation Example 1-1 was used.

TABLE 6

| Components (wt %) | Comparative Example 8 | Comparative Example 9 | Example 10 | Example 11 |
|---|---|---|---|---|
| Synthetic wax, ethylene/propylene copolymer | 5.0 | 5.0 | 5.0 | 5.0 |
| Ceresin | 6.5 | 6.5 | 6.5 | 6.5 |
| Polyglyceryl-2 triisostearate | | Remainder | | |
| Triethylhexanoin | 45.0 | 45.0 | 45.0 | 45.0 |
| Pigment Red No. 104-1 (Red28 Lake) | 0.3 | — | — | — |
| Pigment Red No. 103-1 (Red22 Lake) | — | 0.3 | — | — |
| Coloring material of Example 3 | — | — | 30.0 | — |
| Coloring material of Example 4 | — | — | — | 30.0 |
| HDI/trimethylol hexyllactone crosspolymer, silica | 30.0 | 30.0 | — | — |
| Total | | | | 100 |

As shown in FIGS. 5A and 5B, when lipsticks manufactured in Comparative Examples 8 and 9, in which conventional lake colors were used in anhydrous formulations, and lipsticks manufactured in Preparation Examples 1 and 2, in which the coloring material of Example 3 or 4 of the present invention was used, were compared, color difference was observed by visual observation. In particular, in the cases of Comparative Examples 8 and 9, although the cosmetic composition included an HDI/trimethylol hexyllactone crosspolymer and silica as the polyurethane powder, color difference was significant compared with the lipsticks of Examples 10 and 11. These results indicate that the color expression properties of the surface-modified coloring material of the present invention are not due to simple mixing of a polyamide or a polyurethane powder and a dye.

Preparation Example 3

Preparation of Cosmetic Composition

The kinds of dyes used in preparation of various cosmetic colors and the proportions of the dyes were changed to prepare a makeup cosmetic coloring material by five similar methods. In the same manner as above, a cosmetic composition according to Comparative Example (conventional lake color, marked as "Unmodified" in Table 7) and a cosmetic composition according to Example (novel coloring material of the present invention that was modified with a polyurethane powder according to Preparation Example 1-1, marked as "Modified" in Table 7) were prepared. In five conditions, the value and chroma of the compositions were compared. Table 7 below shows the values of a Munsell color system measured using a MINOLTA CM512M3 color-difference meter.

The contents of colors used in Samples 1 to 5 of Table 7 were the same. As shown in Table 7, it was confirmed that, as compared with the case in which a conventional lake color was included, the value and chroma of the cosmetic composition including the novel cosmetic coloring material according to the present invention were increased. Accordingly, the cosmetic composition including the coloring material of the present invention may have a vivid color and excellent color expression properties.

The invention claimed is:

1. A coloring material, comprising:
one or more selected from the group consisting of a polyurethane powder and a polyamide powder having a weight average molecular weight of 200,000 or more; and
a water-soluble dye represented by Structural Formula 1 below

[Structural Formula 1]

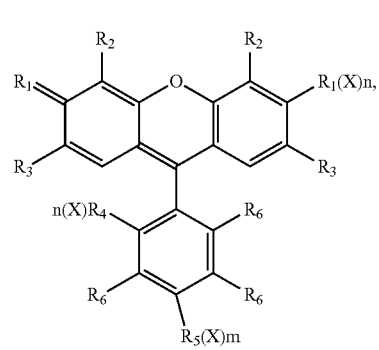

TABLE 7

| Samples (Content is expressed in wt % based on total weight of 100 g) | Value | | Chroma | |
|---|---|---|---|---|
| | Unmodified | Modified | Unmodified | Modified |
| Sample 1 (Unmodified: Pigment Red No. 103-1 Lake 0.3 wt %; Modified: using 30 g of coloring material including 1 wt % of Pigment Red No. 103-1) | 5.66 | 6.84 | 12.48 | 15.93 |
| Sample 2 (Unmodified: Pigment Red No. 103-1 Lake 0.9 wt %; Modified: using 30 g of coloring material including 3 wt % of Pigment Red No. 103-1) | 5.03 | 5.73 | 13.22 | 14.72 |
| Sample 3 (Unmodified: Pigment Red No. 104-1 Lake 0.1 wt %; Modified: using 10 g of coloring material including 1 wt % of Pigment Red No. 104-1) | 4.65 | 6.24 | 13.58 | 17.68 |
| Sample 4 (Unmodified: Pigment Red No. 104-1 Lake 0.6 wt %; Modified: using 30 g of coloring material including 2 wt % of Pigment Red No. 104-1) | 4.32 | 5.46 | 13.03 | 17.54 |
| Sample 5 (Unmodified: Pigment Red No. 104-1 Lake 1.5 wt %; Modified: using 30 g of coloring material including 5 wt % of Pigment Red No. 104-1) | 3.97 | 4.41 | 12.57 | 14.04 | wherein $R_1$ is oxygen (O) or $N(C_2H_5)_2$, wherein, when $R_1$ is oxygen, n is 1, and when $R_1$ is $N(C_2H_5)_2$, n is 0;

$R_2$ and $R_3$ are each independently hydrogen, bromine (Br), or iodine (I);

$R_4$ is $COO^-$ or $SO_3^-$, wherein when $R_4$ is $COO^-$, n is 1, and when $R_4$ is $SO_3^-$, n is 0;

$R_5$ is hydrogen, chlorine, or $SO_3^-$, wherein, when $R_5$ is hydrogen or chlorine, m is 0, and when $R_5$ is $SO_3^-$, m is 1;

$R_6$ is hydrogen or chlorine; and

X is aluminum, calcium, sodium, or potassium.

2. The coloring material according to claim 1, wherein the polyurethane comprises one or more selected from the group consisting of a hexamethylene diisocyanate (HDI)/trimethylol hexyllactone crosspolymer; and a hexamethylene diisocyanate (HDI)/polypropylene glycol (PPG)/polycaprolactone crosspolymer.

3. The coloring material according to claim 1, wherein the polyamide comprises one or more selected from the group consisting of nylon-6, nylon-11, nylon-12, nylon-66, and copolymers thereof.

4. The coloring material according to claim 1, wherein the water-soluble dye comprises one or more selected from the group consisting of Pigment Red No. 104-1, Pigment Red No. 104-2, Pigment Red No. 103-1, Pigment Red No. 230-2, Pigment Orange No. 207, Pigment Red No. 106, Pigment Yellow No. 202-1, and Pigment Yellow No. 202-2.

5. The coloring material according to claim 1, wherein the coloring material has a reflectance of greater than 100.

6. The coloring material according to claim 1, wherein the coloring material comprises a polyurethane powder; and one or more water-soluble dyes selected from the group consisting of Pigment Red No. 104-1, Pigment Red No. 104-2, Pigment Red No. 103-1, Pigment Red No. 230-2, Pigment Orange No. 207, Pigment Red No. 106, Pigment Yellow No. 202-1, and Pigment Yellow No. 202-2.

7. A cosmetic composition, comprising the coloring material according to claim 1.

8. The cosmetic composition according to claim 7, wherein the cosmetic composition is an anhydrous formulation.

9. A cosmetic composition for lips, comprising the coloring material according to claim 1.

* * * * *